United States Patent
Takahashi

(10) Patent No.: US 11,826,596 B2
(45) Date of Patent: Nov. 28, 2023

(54) AZEOTROPIC OR AZEOTROPIC-LIKE COMPOSITION COMPRISING HYDROGEN FLUORIDE AND 1,1,2-TRIFLUOROETHANE, 1-CHLORO-2,2-DIFLUOROETHANE, OR 1,2-DICHLORO-1-FLUOROETHANE

(71) Applicant: DAIKIN INDUSTRIES, LTD., Osaka (JP)

(72) Inventor: Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 44 days.

(21) Appl. No.: 17/496,112

(22) Filed: Oct. 7, 2021

(65) Prior Publication Data

US 2022/0023693 A1   Jan. 27, 2022

Related U.S. Application Data

(63) Continuation of application No. PCT/JP2020/015962, filed on Apr. 9, 2020.

(30) Foreign Application Priority Data

Apr. 10, 2019   (JP) .................. 2019-075126

(51) Int. Cl.
*A62D 1/00* (2006.01)
*B01D 3/14* (2006.01)
(Continued)

(52) U.S. Cl.
CPC ........... *A62D 1/0057* (2013.01); *B01D 3/143* (2013.01); *B01D 3/36* (2013.01); *C07C 17/383* (2013.01);
(Continued)

(58) Field of Classification Search
None
See application file for complete search history.

(56) References Cited

U.S. PATENT DOCUMENTS

| 5,180,860 A | 1/1993 | Fernandez et al. |
| 6,294,055 B2 * | 9/2001 | Herkelmann ........... C07C 17/38 203/44 |

(Continued)

FOREIGN PATENT DOCUMENTS

| EP | 3 919 467 | 12/2021 |
| FR | 3 067 347 | 12/2018 |

(Continued)

OTHER PUBLICATIONS

Horsley; Azeotropic Data—III, Advances in Chemistry; American Chemical Society: Washington, DC, 1973, pp. 11, 94, 99, and 100.
(Continued)

*Primary Examiner* — Joseph D Anthony
(74) *Attorney, Agent, or Firm* — Wenderoth, Lind & Ponack, L.L.P.

(57) ABSTRACT

The present disclosure provides a novel azeotropic or azeotrope-like composition comprising hydrogen fluoride and 1,1,2-trifluoroethane (HFC-143), 1-chloro-2,2-difluoroethane (HCFC-142), or 1,2-dichloro-1-fluoroethane (HCFC-141); and a separation method using the composition.
An azeotropic or azeotrope-like composition comprising hydrogen fluoride and HFC-143. An azeotropic or azeotrope-like composition comprising hydrogen fluoride and HCFC-142. An azeotropic or azeotrope-like composition comprising hydrogen fluoride and HCFC-141. A separation method of a composition comprising hydrogen fluoride and at least one member selected from the group consisting of HFC-143, HCFC-142, and HCFC-141.

1 Claim, 1 Drawing Sheet

(51) Int. Cl.
    *B01D 3/36*     (2006.01)
    *C07C 17/383*     (2006.01)
    *C08J 9/12*     (2006.01)
    *C08J 9/14*     (2006.01)
    *C09K 3/14*     (2006.01)
    *C09K 3/30*     (2006.01)
    *C09K 5/04*     (2006.01)
    *C11D 7/50*     (2006.01)
    *H01B 3/56*     (2006.01)

(52) U.S. Cl.
CPC .............. *C08J 9/127* (2013.01); *C08J 9/146* (2013.01); *C09K 3/1472* (2013.01); *C09K 3/30* (2013.01); *C09K 5/045* (2013.01); *C11D 7/5018* (2013.01); *C11D 7/5036* (2013.01); *H01B 3/56* (2013.01); *C08J 2203/142* (2013.01); *C08J 2203/182* (2013.01); *C09K 2205/122* (2013.01); *C09K 2205/22* (2013.01); *C09K 2205/32* (2013.01)

(56) References Cited

U.S. PATENT DOCUMENTS

| | | | |
|---|---|---|---|
| 7,608,574 B2* | 10/2009 | Cottrell | C07C 19/08 570/178 |
| 2016/0023176 A1* | 1/2016 | Bonnet | H01B 3/56 252/75 |
| 2017/0267612 A1 | 9/2017 | Bonnet et al. | |
| 2018/0126348 A1* | 5/2018 | Bonnet | C09K 3/30 |
| 2020/0002253 A1 | 1/2020 | Garrait et al. | |
| 2020/0157027 A1 | 5/2020 | Wendlinger et al. | |
| 2021/0163381 A1 | 6/2021 | Komatsu | |
| 2021/0346820 A1* | 11/2021 | Takahashi | C01B 7/196 |
| 2022/0098132 A1 | 3/2022 | Wendlinger et al. | |

FOREIGN PATENT DOCUMENTS

| | | |
|---|---|---|
| JP | 2016-130236 | 7/2016 |
| JP | 2017-501992 | 1/2017 |
| WO | 94/11460 | 5/1994 |
| WO | 2017/104828 | 6/2017 |
| WO | 2018/060576 | 4/2018 |
| WO | 2018/069609 | 4/2018 |
| WO | 2019/216239 | 11/2019 |

OTHER PUBLICATIONS

International Search Report dated Jul. 7, 2020 in International (PCT) Application No. PCT/JP2020/015962.
McBee et al., "Fluorinated Derivatives of Ethane", Industrial and Engineering Chemistry, 1947, vol. 39, No. 3, pp. 409-412.
Extended European Search Report dated Jun. 15, 2023 in corresponding European Patent Application No. 20787991.7.

* cited by examiner

AZEOTROPIC OR AZEOTROPIC-LIKE COMPOSITION COMPRISING HYDROGEN FLUORIDE AND 1,1,2-TRIFLUOROETHANE, 1-CHLORO-2,2-DIFLUOROETHANE, OR 1,2-DICHLORO-1-FLUOROETHANE

TECHNICAL FIELD

The present disclosure relates to an azeotropic or azeotrope-like composition comprising 1,1,2-trifluoroethane, 1-chloro-2,2-difluoroethane, or 1,2-dichloro-1-fluoroethane, and hydrogen fluoride; and a separation method of hydrogen fluoride using the properties of the composition.

BACKGROUND ART

It is said that 1,1,2-trifluoroethane (HFC-143) is useful as a foaming agent for polyolefins and polyurethanes, an aerosol propellant, a refrigerant, a heat transfer medium, a gaseous dielectric, a fire-extinguishing agent, a power cycle working fluid, a polymerization medium, a particulate removal fluid, a carrier fluid, a buffing abrasive agent, and a displacement drying agent (Patent Literature 1). HFC-143 has a boiling point of about 4° C.

CITATION LIST

Patent Literature

PTL 1: WO94/011460

SUMMARY

Solution to Problem

An azeotropic or azeotrope-like composition comprising 1,1,2-trifluoroethane (HFC-143) and hydrogen fluoride.

Advantageous Effects

The present disclosure provides a novel azeotropic or azeotrope-like composition comprising 1,1,2-trifluoroethane, 1-chloro-2,2-difluoroethane, or 1,2-dichloro-1-fluoroethane, and hydrogen fluoride; and a separation method using the composition.

DESCRIPTION OF EMBODIMENTS

Figure 1:
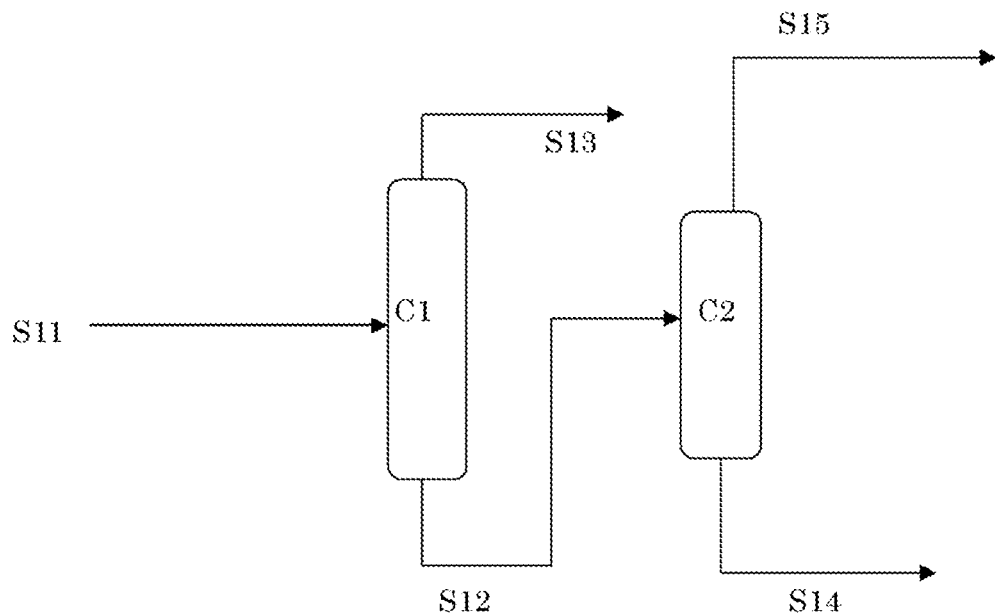
FIG. 1 is a diagram showing an example of a separation method that uses an azeotropic or azeotrope-like composition.

In the present specification, the term "azeotrope-like composition" refers to a composition that can be treated substantially as an azeotropic composition. More specifically, the term "azeotrope-like composition" as used herein refers to a constant boiling mixture or a substantially constant boiling mixture of two or more substances that behave substantially as a single substance. One of the characteristics of azeotrope-like compositions is that the formulation of vapor generated by evaporation or distillation of a liquid substantially does not undergo a change from the formulation of the liquid. That is, in the present specification, a mixture that boils, distills, or refluxes without substantial change in formulation is referred to as an "azeotrope-like composition." More specifically, in the present disclosure, a composition is defined as an azeotrope-like composition when the difference between the bubble point vapor pressure of the composition and the dew point vapor pressure of the composition at a specific temperature is 3% or less (based on the bubble point pressure).

In the present specification, an azeotropic composition and an azeotrope-like composition in which the liquid phase separates into two liquid phases are respectively referred to as a heterophase azeotropic composition and a heterophase azeotrope-like composition.

HFC-143 can be produced, for example, by a fluorination reaction using 1-chloro-2,2-difluoroethane (HCFC-142) or 1,2-dichloro-1-fluoroethane (HCFC-141) as a raw material. The inventor focused on the fact that in the conventional production methods of HFC-143, not all of the raw materials used are converted into target products; and intermediates and unreacted raw materials must be separated, collected, and recycled by a certain method. This is because these raw materials, if not collected, will be wasted, which leads to increased costs.

The inventor found that combinations of the specific components contained in these raw materials form azeotropic or azeotrope-like compositions; and further found that these compositions are useful in separation based on a method such as distillation, extraction, or liquid-liquid separation. The present disclosure has thus been completed.

1. Composition 1

Composition 1 is an azeotropic or azeotrope-like composition comprising HFC-143 and hydrogen fluoride (HF).

In Composition 1, from the viewpoint of collecting unreacted hydrogen fluoride to increase the yield, it is preferable to contain HFC-143 in an amount of 40 mass % or more to less than 100 mass %, more preferably 50 mass % or more to less than 100 mass %, and even more preferably 60 mass % or more to less than 100 mass %, based on the total amount of HFC-143 and hydrogen fluoride defined as 100 mass %.

For example, when composition 1 comprises HFC-143 in an amount of 68 mol % (90 mass %) based on the total amount of HFC-143 and hydrogen fluoride defined as 100 mol % (100 mass %), at 40° C. and a pressure of 539 kPa, it becomes an azeotropic composition (heterophase azeotropic composition). When composition 1, for example, comprises HFC-143 in an amount of 20 mol % or more to 95 mol % or less (51 mass % or more to 99 mass % or less) based on the total amount of HFC-143 and hydrogen fluoride defined as 100 mol % (100 mass %), at 40° C. and a pressure of 524 to 554 kPa, it becomes an azeotrope-like composition. The above pressure is in the range of pressure at which an azeotropic and azeotrope-like composition is provided (at 40° C.).

The mass % and mol % above indicate the values in the liquid phase.

In the present specification, the pressure refers to absolute pressure, unless otherwise specified.

Composition 1 may further comprise an additional compound, in addition to HFC-143 and hydrogen fluoride.

The additional compound is not limited, and can be broadly selected, as long as it does not interfere with composition 1 becoming an azeotropic or azeotrope-like composition. The additional compounds may be used singly, or in a combination of two or more.

Examples of the additional compound include 1,1,2-trifluoroethylene (HFC-1123), 1,1-difluoromethane (HFC-152a), fluoroethane (HFC-161), 1-chloro-1,2,2-trifluoromethane (HCFC-133), 2-chloro-1,1,1-trifluoroethane (HCFC-133a), 1-chloro-1,1,2-trifluoroethane (HCFC-133b), 2,2-dichloro-1,1,1-trifluoroethane (HCFC-123), and 1,2-difluoroethane (HFC-152).

The total amount thereof can be suitably selected as long as it does not interfere with composition 1 becoming an azeotropic or azeotrope-like composition.

When the additional compound is contained, the total amount thereof is preferably more than 0 mass % to 1 mass % or less, more preferably more than 0 mass % to 0.5 mass % or less, and even more preferably more than 0 mass % to 0.1 mass % or less, based on the entire composition 1 defined as 100 mass %.

Composition 1 can serve as an important composition when azeotropic distillation of a mixture of HFC-143 and hydrogen fluoride is performed to separate hydrogen fluoride from HFC-143.

For example, hydrogen fluoride can be separated from HFC-143 by extracting an azeotropic or azeotrope-like composition that comprises HFC-143 and hydrogen fluoride from a composition that comprises at least HFC-143 and hydrogen fluoride by azeotropic distillation. HF remaining in the extracted azeotropic or azeotrope-like composition can be separated and collected by using a method such as absorption (extraction) with $H_2SO_4$ or water-washing.

The azeotropic distillation is a method of concentration or separation of a target product by operating a distillation column under conditions in which an azeotropic or azeotrope-like composition is separated. In some cases, azeotropic distillation can allow distillation of only the target component for separation. In other cases, however, azeotropic distillation occurs only when another component that forms an azeotropic mixture with one or more of the target components for separation is added from the outside. In the present specification, both the former and the latter cases are referred to as "azeotropic distillation."

2. Composition 2

Composition 2 is an azeotropic or azeotrope-like composition comprising HCFC-142 and hydrogen fluoride (HF).

In Composition 2, from the viewpoint of collecting unreacted hydrogen fluoride to increase the yield, it is preferable to contain HCFC-142 in an amount of 10 mass % or more to 99 mass % or less, more preferably 20 mass % or more to 99 mass % or less, and even more preferably 36 mass % or more to 99 mass % or less, based on the total amount of HCFC-142 and hydrogen fluoride defined as 100 mass %.

For example, when composition 2 comprises HCFC-142 in an amount of 36.2 mol % (74 mass %) based on the total amount of HCFC-142 and hydrogen fluoride defined as 100 mol % (100 mass %), at 40° C. and a pressure of 281 kPa, it becomes an azeotropic composition (heterophase azeotropic composition). When composition 2, for example, comprises HCFC-142 in an amount of 10 mol % or more to 95 mol % or less (36 mass % or more to 99 mass % or less) based on the total amount of HCFC-142 and hydrogen fluoride defined as 100 mol % (100 mass %), it becomes an azeotrope-like composition at 40° C. and a pressure of 272 to 290 kPa. The above pressure is in the range of pressure at which an azeotropic and azeotrope-like composition is provided (at 40° C.).

The mass % and mol % above indicate the values in the liquid phase.

Composition 2 may further comprise an additional compound, in addition to HCFC-142 and hydrogen fluoride.

The additional compound is not limited, and can be broadly selected as long as it does not interfere with composition 2 becoming an azeotropic or azeotrope-like composition. The additional compounds may be used singly, or in a combination of two or more.

Examples of the additional compound include 1,1,2-trifluoroethylene (HFC-1123), 1,1-difluoromethane (HFC-152a), fluoroethane (HFC-161), 1,1,2-trifluoroethane (HFC-143), 1-chloro-1,2,2-trifluoromethane (HCFC-133), 2-chloro-1,1,1-trifluoroethane (HCFC-133a), 1-chloro-1,1,2-trifluoroethane (HCFC-133b), 2,2-dichloro-1,1,1-trifluoroethane (HCFC-123), and 1,2-difluoroethane (HFC-152).

The total amount thereof can be suitably selected as long as it does not interfere with composition 2 becoming an azeotropic or azeotrope-like composition.

When the additional compound is contained, the total amount thereof is preferably more than 0 mass % to 1 mass % or less, more preferably more than 0 mass % to 0.5 mass % or less, and even more preferably more than 0 mass % to 0.1 mass % or less, based on the entire composition 2 defined as 100 mass %.

Composition 2 can serve as an important composition when azeotropic distillation of a mixture of HCFC-142 and hydrogen fluoride is performed to separate hydrogen fluoride from HCFC-142.

For example, hydrogen fluoride can be separated from HCFC-142 by extracting an azeotropic or azeotrope-like composition that comprises HCFC-142 and hydrogen fluoride from a composition that comprises at least HCFC-142 and hydrogen fluoride by azeotropic distillation. HF remaining in the extracted azeotropic or azeotrope-like composition can be separated and collected by using a method such as absorption (extraction) with $H_2SO_4$ or water-washing.

3. Composition 3

Composition 3 is an azeotropic or azeotrope-like composition comprising HCFC-141 and hydrogen fluoride (HF).

In composition 3, from the viewpoint of collecting unreacted hydrogen fluoride to increase the yield, it is preferable to contain HCFC-141 in an amount of 20 mass % or more to 99 mass % or less, more preferably 30 mass % or more to 99 mass % or less, and even more preferably 39 mass % or more to 99 mass % or less, based on the total amount of HCFC-141 and hydrogen fluoride defined as 100 mass %.

For example, when composition 3 comprises HCFC-141 in an amount of 42.9 mol % (81 mass %) based on the total amount of HCFC-141 and hydrogen fluoride defined as 100 mol % (100 mass %), it becomes an azeotropic composition (heterophase azeotropic composition) at 40° C. and a pressure of 196 kPa. When composition 3, for example, comprises HCFC-141 in an amount of 10 mol % or more to 95 mol % or less (39 mass % or more to 99 mass % or less) based on the total amount of HCFC-141 and hydrogen fluoride defined as 100 mol % (100 mass %), it becomes an azeotrope-like composition at 40° C. and a pressure of 190 to 202 kPa.

The above pressure is in the range of pressure at which an azeotropic and azeotrope-like composition is provided (at 40° C.).

The mass % and mol % above indicate the values in the liquid phase.

Composition 3 may further comprise an additional compound in addition to HCFC-141 and hydrogen fluoride.

The additional compound is not limited, and can be broadly selected as long as it does not interfere with composition 3 becoming an azeotropic or azeotrope-like composition. The additional compounds may be used singly, or in a combination of two or more.

Examples of the additional compound include 1,1,2-trifluoroethylene (HFC-1123), 1,1-difluoromethane (HFC-152a), fluoroethane (HFC-161), 1,1,2-trifluoroethane (HFC-143), 1-chloro-1,2,2-trifluoromethane (HCFC-133), 2-chloro-1,1,1-trifluoroethane (HCFC-133a), 1-chloro-1,1, 2-trifluoroethane (HCFC-133b), 2,2-dichloro-1,1,1-trifluoroethane (HCFC-123), and 1,2-difluoroethane (HFC-152).

The total amount thereof can be suitably selected as long as it does not interfere with composition 3 becoming an azeotropic or azeotrope-like composition.

When the additional compound is contained, the total amount thereof is preferably more than 0 mass % to 1 mass % or less, more preferably more than 0 mass % to 0.5 mass % or less, and even more preferably more than 0 mass % to 0.1 mass % or less, based on the entire composition 3 defined as 100 mass %.

Composition 3 can serve as an important composition when azeotropic distillation of a mixture of HCFC-141 and hydrogen fluoride is performed to separate hydrogen fluoride from HCFC-141.

For example, hydrogen fluoride can be separated from HCFC-141 by extracting an azeotropic or azeotrope-like composition that comprises HCFC-141 and hydrogen fluoride from a composition that comprises at least HCFC-141 and hydrogen fluoride by azeotropic distillation. HF remaining in the extracted azeotropic or azeotrope-like composition can be separated and collected by using a method such as absorption (extraction) with $H_2SO_4$ or water-washing.

4. Separation Method

The present disclosure also discloses a separation method of each component using the composition described above.

The separation method according to the present disclosure is a separation method of a composition comprising hydrogen fluoride, and at least one member selected from the group consisting of 1,1,2-trifluoroethane (HFC-143), 1-chloro-2,2-difluoroethane (HCFC-142), and 1,2-dichloro-1-fluoroethane (HCFC-141), the method comprising steps (a) and (b), and optionally further comprising steps (c) and (d):

(a) supplying a composition comprising hydrogen fluoride and at least one member selected from the group consisting of HFC-143, HCFC-142, and HCFC-141 to a first distillation column;

(b) obtaining, as a first distillate, an azeotropic or azeotrope-like composition comprising hydrogen fluoride and at least one member selected from the group consisting of HFC-143, HCFC-142, and HCFC-141, and extracting, as a bottom composition of the first distillation column, a composition that is more enriched in either i) at least one member selected from the group consisting of HFC-143, HCFC-142, and HCFC-141, or ii) hydrogen fluoride, in terms of the concentration, than the supplied composition;

(c) supplying the bottom composition of the first distillation column to a second distillation column having a different operation temperature and/or operation pressure to perform distillation; and (d) if the composition extracted as the bottom composition of the first distillation column is more enriched in hydrogen fluoride in terms of the concentration than a supplied stream, extracting a stream having a richer hydrogen fluoride concentration as a bottom composition of the second distillation column, and if the composition extracted as the bottom composition of the first distillation column is more enriched in at least one member selected from the group consisting of HFC-143, HCFC-142, and HCFC-141 in terms of the concentration than the supplied stream, extracting a stream having a richer concentration of at least one member selected from the group consisting of HFC-143, HCFC-142, and HCFC-141 as a bottom composition of the second distillation column.

The above separation method is a separation method comprising the step of separating a composition comprising hydrogen fluoride and at least one member selected from the group consisting of HFC-143, HCFC-142, and HCFC-141, into at least one member selected from the group consisting of HFC-143, HCFC-142, and HCFC-141 and hydrogen fluoride. This method involves distillation separation using the properties of HFC-143, HCFC-142, and HCFC-141, and hydrogen fluoride becoming an azeotropic or azeotrope-like composition.

For example, by extracting an azeotropic or azeotrope-like composition comprising at least hydrogen fluoride and HFC-143, HCFC-142, or HCFC-141 from a composition comprising hydrogen fluoride and at least HFC-143, HCFC-142, or HCFC-141, hydrogen fluoride can be separated from HFC-143, HCFC-142, or HCFC-141.

As described in the Examples below, distillation separation can be performed for a composition comprising HFC-143, HCFC-142, and HCFC-141, and hydrogen fluoride using the properties of each of the above components becoming an azeotropic or azeotrope-like composition.

In the separation method, the composition comprising hydrogen fluoride, and at least one member selected from the group consisting of HFC-143, HCFC-142, and HCFC-141 as a starting composition for use in step (a) may be a composition consisting of hydrogen fluoride and at least one member selected from the group consisting of HFC-143, HCFC-142, and HCFC-141; or may be a composition further comprising other components in addition to hydrogen fluoride and at least one member selected from the group consisting of HFC-143, HCFC-142, and HCFC-141.

In step (b) above, the concentration of either i) or ii) in the composition obtained after the first distillate has been distilled from the supplied composition is higher than the concentration in the supplied composition (because the total amount and the formulation of the composition undergo a change). The composition that is more enriched in either i) or ii) in terms of the concentration than the supplied composition is extracted as the bottom composition of the first distillation column.

In the above step (c), the bottom composition of the first distillation column is supplied to a second distillation column having a different operation temperature and/or operation pressure to perform distillation. The operating conditions (operating temperature and/or operating pressure) for each of the first and second distillation columns can be appropriately set. In terms of the efficiency of distillation and the like, the operating conditions for the second distillation column are preferably different from those for the first distillation column.

In step (d), if the composition extracted as the bottom composition of the first distillation column is more enriched in hydrogen fluoride in terms of the concentration than a supplied stream, a stream having a richer hydrogen fluoride concentration is extracted as a bottom composition of the second distillation column, and if the composition extracted as the bottom composition of the first distillation column is more enriched in at least one member selected from the group consisting of HFC-143, HCFC-142, and HCFC-141 in terms of the concentration than the supplied stream, a stream having a richer concentration of at least one member selected from the group consisting of HFC-143, HCFC-142, and HCFC-141 is extracted as a bottom composition of the second distillation column.

The "supplied stream" in step (d) is a stream that is supplied to the first distillation column in step (a).

In the separation method described above, steps (c) and (d) are not essential steps, and are optional. The separation method may be a method that consists of steps (a) and (b) above, a method that consists of steps (a) to (d) above, or a method that further comprises other steps in addition to steps (a) to (d) above.

Figure 2:
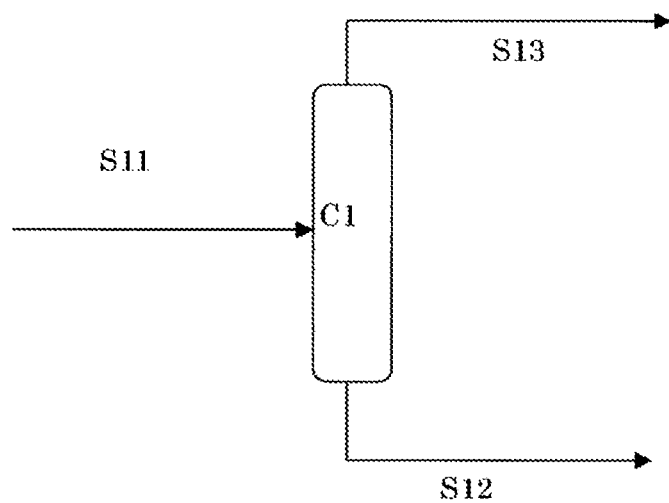
FIG. 2 is a diagram showing another example of a separation method that uses an azeotropic or azeotrope-like composition.

FIG. 1 shows an example of the separation method, and FIG. 2 shows another example.

In FIG. 1, C1 represents a first distillation column and C2 represents a second distillation column; a composition is supplied from S11 to C1, the first distillate is obtained from S13, the bottom composition of the first distillation column is extracted from S12, and supplied to C2, the second distillate is obtained from S15, and the bottom composition of the second distillation column is extracted from S14.

In FIG. 2, C1 represents a first distillation column; a composition is supplied from S11 to C1, the first distillate is obtained from S13, and the bottom composition of the first distillation column is extracted from S12.

Specific examples are as follows.

The composition comprising hydrogen fluoride, and HFC-143, HCFC-142, or HCFC-141 is supplied from S11 to distillation column C1. The azeotropic composition of HFC-143 and hydrogen fluoride is distilled off from S13; and HCFC-142, HCFC-141, and hydrogen fluoride are obtained from S12.

S13 is sent to the next step, where liquid-liquid separation is performed to separate a phase enriched in HF and a phase enriched in HFC-143. The phase enriched in HF is recycled to the reaction step (HFC-143 production step). The phase enriched in HFC-143 can be made into a product by completely removing a very small amount of remaining HF by washing with water and an alkali aqueous solution; or by means not using water, e.g., absorption with $H_2SO_4$.

The obtained HCFC-142, HCFC-141, and hydrogen fluoride are supplied from S12 to C2. In C2, as in C1, distillation using an azeotropic or azeotrope-like composition is performed to separate stream S15 mainly comprising an azeotropic or azeotrope-like composition of HCFC-142 and hydrogen fluoride from stream S14 mainly comprising HCFC-141 and hydrogen fluoride. Each stream can also be recycled to the reaction step (HFC-143 production step).

The small amount of HF extracted together as an azeotropic or azeotrope-like composition can be recovered using other general-purpose methods (absorption by water) in combination, whereby the loss can be minimized, and the burden on the equipment can be reduced. Each compound and HF can all be reused as raw materials for the reaction by using a recovery method of HF without using water, such as absorption by $H_2SO_4$. This can minimize the equipment for recovery using corrosive $H_2SO_4$, and thus can reduce equipment costs.

As described above, the separation method according to the present disclosure is capable of efficiently separating hydrogen fluoride.

The embodiments are described above; however, it can be understood that various changes in forms and details can be made without departing from the spirit and scope of the claims.

Item 1. An azeotropic or azeotrope-like composition comprising 1,1,2-trifluoroethane (HFC-143) and hydrogen fluoride.

Item 2. The azeotropic or azeotrope-like composition according to Item 1, wherein the HFC-143 is present in an amount of 40 mass % or more to less than 100 mass %, based on the total amount of the HFC-143 and the hydrogen fluoride defined as 100 mass %.

Item 3. An azeotropic or azeotrope-like composition comprising 1-chloro-2,2-difluoroethane (HCFC-142) and hydrogen fluoride.

Item 4. The azeotropic or azeotrope-like composition according to Item 3, wherein the HCFC-142 is present in an amount of 10 mass % or more to 99 mass % or less, based on the total amount of the HCFC-142 and the hydrogen fluoride defined as 100 mass %.

Item 5. An azeotropic or azeotrope-like composition comprising 1,2-dichloro-1-fluoroethane (HCFC-141) and hydrogen fluoride.

Item 6. The azeotropic or azeotrope-like composition according to Item 5, wherein the HCFC-141 is present in an amount of 20 mass % or more to 99 mass % or less, based on the total amount of the HCFC-141 and the hydrogen fluoride defined as 100 mass %.

Item 7. A separation method of a composition comprising hydrogen fluoride and at least one member selected from the group consisting of 1,1,2-trifluoroethane (HFC-143), 1-chloro-2,2-difluoroethane (HCFC-142), and 1,2-dichloro-1-fluoroethane (HCFC-141),
the method comprising steps (a) and (b), and optionally further comprising steps (c) and (d):
(a) supplying a composition comprising hydrogen fluoride and at least one member selected from the group consisting of HFC-143, HCFC-142, and HCFC-141 to a first distillation column;
(b) obtaining, as a first distillate, an azeotropic or azeotrope-like composition comprising hydrogen fluoride and at least one member selected from the group consisting of HFC-143, HCFC-142, and HCFC-141, and extracting, as a bottom composition of the first distillation column, a composition that is more enriched in either i) at least one member selected from the group consisting of HFC-143, HCFC-142, and HCFC-141, or ii) hydrogen fluoride, in terms of the concentration, than the supplied composition;
(c) supplying the bottom composition of the first distillation column to a second distillation column having a different operation temperature and/or operation pressure to perform distillation; and
(d) if the composition extracted as the bottom composition of the first distillation column is more enriched in hydrogen fluoride in terms of the concentration than a supplied stream, extracting a stream having a richer hydrogen fluoride concentration as a bottom composition of the second distillation column, and if the composition extracted as the bottom composition of the first distillation column is more enriched in at least one member selected from the group consisting of HFC-143, HCFC-142, and HCFC-141 in terms of the concentration than the supplied stream, extracting a stream having a richer concentration of at least one member selected from the group consisting of HFC-143, HCFC-142, and HCFC-141 as the bottom composition of the second distillation column.

EXAMPLES

The present disclosure is described in more detail below with reference to Examples. However, the present disclosure is not limited to the Examples.

Example 1

Tables 1 to 3 show vapor-liquid equilibrium data for mixtures of HFC-143, HCFC-142, or HCFC-141 with hydrogen fluoride (HF) at 40° C. The numerical units in the tables for each compound in the liquid phase and gas phase are molar ratios (in each of the liquid phase and the gas phase, the total number of moles of each compound and HF is defined as 1).

TABLE 1

| Liquid phase HFC-143 molar ratio | Liquid phase HF molar ratio | Gas phase HFC-143 molar ratio | Gas phase HF molar ratio | Total pressure (MPa) |
|---|---|---|---|---|
| 0.05 | 0.95 | 0.411 | 0.589 | 0.321 |
| 0.10 | 0.90 | 0.620 | 0.380 | 0.469 |
| 0.20 | 0.80 | 0.679 | 0.321 | 0.539 |
| 0.30 | 0.70 | 0.680 | 0.320 | 0.539 |
| 0.40 | 0.60 | 0.680 | 0.320 | 0.539 |
| 0.50 | 0.50 | 0.680 | 0.320 | 0.539 |
| 0.60 | 0.40 | 0.680 | 0.320 | 0.539 |
| 0.68 | 0.32 | 0.680 | 0.320 | 0.539 |
| 0.70 | 0.30 | 0.680 | 0.320 | 0.539 |
| 0.80 | 0.20 | 0.680 | 0.320 | 0.539 |
| 0.90 | 0.10 | 0.680 | 0.320 | 0.539 |
| 0.95 | 0.05 | 0.680 | 0.320 | 0.539 |
| 0.99 | 0.01 | 0.818 | 0.182 | 0.453 |

TABLE 2

| Liquid phase HCFC-142 molar ratio | Liquid phase HF molar ratio | Gas phase HCFC-142 molar ratio | Gas phase HF molar ratio | Total pressure (MPa) |
|---|---|---|---|---|
| 0.99 | 0.01 | 0.516 | 0.484 | 0.200 |
| 0.95 | 0.05 | 0.362 | 0.638 | 0.281 |
| 0.90 | 0.10 | 0.362 | 0.638 | 0.281 |
| 0.80 | 0.20 | 0.362 | 0.638 | 0.281 |
| 0.70 | 0.30 | 0.362 | 0.638 | 0.281 |
| 0.362 | 0.638 | 0.362 | 0.638 | 0.281 |
| 0.60 | 0.40 | 0.362 | 0.638 | 0.281 |
| 0.50 | 0.50 | 0.362 | 0.638 | 0.281 |
| 0.40 | 0.60 | 0.362 | 0.638 | 0.281 |
| 0.30 | 0.70 | 0.362 | 0.638 | 0.281 |
| 0.20 | 0.80 | 0.362 | 0.638 | 0.281 |
| 0.10 | 0.90 | 0.362 | 0.638 | 0.281 |
| 0.05 | 0.95 | 0.211 | 0.789 | 0.239 |
| 0.01 | 0.99 | 0.030 | 0.970 | 0.206 |

TABLE 3

| Liquid phase HCFC-141 molar ratio | Liquid phase HF molar ratio | Gas phase HCFC-141 molar ratio | Gas phase HF molar ratio | Total pressure (MPa) |
|---|---|---|---|---|
| 0.99 | 0.01 | 0.446 | 0.554 | 0.188 |
| 0.95 | 0.05 | 0.429 | 0.571 | 0.196 |
| 0.90 | 0.10 | 0.429 | 0.571 | 0.196 |
| 0.80 | 0.20 | 0.429 | 0.571 | 0.196 |
| 0.70 | 0.30 | 0.429 | 0.571 | 0.196 |
| 0.60 | 0.40 | 0.429 | 0.571 | 0.196 |
| 0.50 | 0.50 | 0.429 | 0.571 | 0.196 |
| 0.429 | 0.571 | 0.429 | 0.571 | 0.196 |
| 0.40 | 0.60 | 0.429 | 0.571 | 0.196 |
| 0.30 | 0.70 | 0.429 | 0.571 | 0.196 |
| 0.20 | 0.80 | 0.429 | 0.571 | 0.196 |
| 0.10 | 0.90 | 0.429 | 0.571 | 0.196 |
| 0.05 | 0.95 | 0.337 | 0.663 | 0.173 |
| 0.01 | 0.99 | 0.049 | 0.951 | 0.127 |

Table 1 shows that when a composition of HFC-143 and HF comprises 68 mol % (90 mass %) of HFC-143 in the liquid phase, the composition becomes an azeotropic composition (heterophase azeotropic composition) when the formulation of the liquid phase and the formulation of the gas phase are the same; and the composition becomes an azeotrope-like composition when it comprises 20 to 95 mol % (51 to 99 mass %) of HFC-143.

Table 2 shows that when a composition of HCFC-142 and HF comprises 36.2 mol % (74 mass %) of HCFC-142 in the liquid phase, the composition becomes an azeotropic composition (heterophase azeotropic composition) when the formulation of the liquid phase and the formulation of the gas phase are the same; and the composition becomes an azeotrope-like composition when it comprises 10 to 95 mol % (36 to 99 mass %) of HCFC-142.

Table 3 shows that when a composition of HCFC-141 and HF comprises 42.9 mol % (81 mass %) of HCFC-141 in the liquid phase, the composition becomes an azeotropic composition (heterophase azeotropic composition) when the formulation of the liquid phase and the formulation of the gas phase are the same; and the composition becomes an azeotrope-like composition when it comprises 10 to 95 mol % (39 to 99 mass %) of HCFC-141.

Accordingly, the cases in which in the vapor-liquid equilibrium data at 40° C., HFC-143 is present in an amount of 20 to 95 mol % in a composition of HFC-143 and HF; HCFC-142 is present in an amount of 10 to 95 mol % in a composition of HCFC-142 and HF; and HCFC-141 is present in an amount of 10 to 95 mol % in a composition of HCFC-141 and HF correspond to the case in which the difference between the bubble point vapor pressure and the dew point vapor pressure of each of these compositions at 40° C. is 3% or less, indicating that these compositions were azeotrope-like compositions.

The above results demonstrate that HFC-143, HCFC-142, and HCFC-141 each form an azeotropic or azeotrope-like composition with HF. These compositions serve as important compositions in separation of HF using a distillation column.

Example 2

A separation method of hydrogen fluoride from at least one member selected from the group consisting of HFC-143, HCFC-142, and HCFC-141 was performed as follows.

FIG. 1 shows an example of a separation method that uses an azeotropic or azeotrope-like composition. Table 4 shows the flow rates of HFC-143, HCFC-142, HCFC-141, and hydrogen fluoride in S11 to S15 of FIG. 1.

TABLE 4

| | Flow rate (kg/hr) | | | | |
|---|---|---|---|---|---|
| | S11 | S12 | S13 | S14 | S15 |
| HF | 2.49 | 2.43 | 0.06 | 1.75 | 0.68 |
| HFC-143 | 0.11 | 0.00 | 0.11 | 0.00 | 0.00 |
| HCFC-142 | 1.00 | 1.00 | 0.00 | 0.00 | 1.00 |
| HCFC-141 | 0.14 | 0.14 | 0.00 | 0.00 | 0.14 |

The composition comprising hydrogen fluoride, and HFC-143, HCFC-142, or HCFC-141 is supplied from S11 to distillation column C1. The azeotropic composition of HFC-143 and hydrogen fluoride is distilled off from S13; and HCFC-142, HCFC-141, and hydrogen fluoride are obtained from S12.

S13 is sent to the next step, where liquid-liquid separation is performed to separate a phase enriched in HF from a phase enriched in HFC-143. The phase enriched in HF is recycled to the reaction step (HFC-143 production step). The phase enriched in HFC-143 can be made into a product by completely removing a very small amount of remaining HF by washing with water and an alkali aqueous solution; or by means that do not use water, e.g., absorption with $H_2SO_4$.

The obtained HCFC-142, HCFC-141, and hydrogen fluoride are supplied from S12 to C2. In C2, as in C1, distillation using an azeotropic or azeotrope-like composition is performed to separate stream S15 mainly comprising an azeotropic or azeotrope-like composition of HCFC-142 and hydrogen fluoride from stream S14 mainly comprising hydrogen fluoride. Each stream can also be recycled to the reaction step (HFC-143 production step).

Alternatively, a liquid-liquid separation process can be used instead of distillation. The composition comprising HCFC-142, HCFC-141, and hydrogen fluoride obtained from S12 is subjected to liquid-liquid separation in the range from −40° C. to 40° C. to separate a phase enriched mainly in HF from a phase enriched mainly in organic matter (HCFC-142, HCFC-141), each of which can be recycled to the reaction step (HFC-143 production step).

The separation operation by the above distillation can also control the reaction conditions (contact time, hydrogen fluoride/organic matter molar ratio) in the reaction step, and can maintain excellent reaction and catalytic activity.

The invention claimed is:

1. An azeotropic or azeotrope-like composition comprising 1,1,2-trifluoroethane (HFC-143) and hydrogen fluoride, wherein the HFC-143 is present in an amount of 40 mass % or more to less than 100 mass %, based on the total amount of the HFC-143 and the hydrogen fluoride defined as 100 mass %.

* * * * *